United States Patent [19]

Bhasin

[11] Patent Number: 5,057,481
[45] Date of Patent: Oct. 15, 1991

[54] CATALYST COMPOSITION FOR OXIDATION OF ETHYLENE TO ETHYLENE OXIDE

[75] Inventor: Madan M. Bhasin, Charleston, W. Va.

[73] Assignee: Union Carbide Chemicals and Plastics Technology Corporation, Danbury, Conn.

[21] Appl. No.: 251,814

[22] Filed: Oct. 3, 1988

Related U.S. Application Data

[63] Continuation-in-part of Ser. No. 18,809, Feb. 20, 1987, abandoned, which is a continuation of Ser. No. 640,269, Aug. 13, 1984, abandoned.

[51] Int. Cl.$^5$ .................. B01J 21/04; B01J 23/04; B01J 23/50
[52] U.S. Cl. .................. 502/208; 502/218; 502/224; 502/317; 502/324; 502/347; 502/348; 549/536
[58] Field of Search ............... 502/208, 218, 317, 324, 502/347, 348, 224; 549/536

[56] References Cited

U.S. PATENT DOCUMENTS

| | | | |
|---|---|---|---|
| 4,761,394 | 8/1988 | Lauritzen | 502/348 |
| 4,808,738 | 2/1989 | Lauritzen | 549/536 |
| 4,820,675 | 4/1989 | Lauritzen | 502/216 |

FOREIGN PATENT DOCUMENTS

| | | |
|---|---|---|
| 247414 | 2/1987 | European Pat. Off. . |
| 266015 | 4/1988 | European Pat. Off. . |
| 266852 | 11/1988 | European Pat. Off. . |
| 56-105750 | 8/1981 | Japan . |
| 57-21937 | 2/1982 | Japan . |
| 2043481 | 10/1980 | United Kingdom . |

Primary Examiner—W. J. Shine
Attorney, Agent, or Firm—Sharon H. Hegedus

[57] ABSTRACT

This invention relates to the catalysts for the manufacture of ethylene oxide at commercial concentrations in the presence of carbon dioxide gas recycle which contains impregnated silver on a support and a mixture of cesium salts, at least one of which is a cesium salt in which the anions thereof are oxyanions of elements having an atomic number of 21 to 75 and being from groups 3b through 7b, inclusive, of the Periodic Table of the Elements.

30 Claims, No Drawings

CATALYST COMPOSITION FOR OXIDATION OF ETHYLENE TO ETHYLENE OXIDE

This is a continuation-in part of U.S. Ser. No. 18,809, filed Feb. 20, 1987, now abandoned, which is a continuation of U.S. Ser. No. 640,269, filed Aug. 13, 1984, now abandoned, both of which are herein incorporated by reference. This application is related to U.S. Ser. No. 251,573, filed on even date herewith, herein incorporated by reference.

BRIEF SUMMARY OF THE INVENTION

This invention relates to catalysts for the manufacture of ethylene oxide, especially at commercial concentrations in the presence of carbon dioxide gas recycle, which contain impregnated silver on a support having a mixture of cesium salts, at least one of which is a cesium salt in which the anions thereof are oxyanions of elements having an atomic number of 21 to 75 and being from groups 3b through 7b, inclusive, of the Periodic Table of the Elements.

SUMMARY ANALYSIS OF PRIOR ART

A number of theories abound about the mechanism of the reaction of ethylene and oxygen. It is sufficient to say that none is universally accepted. What appears to be accepted is that oxygen in some fashion combines with solid silver and through that combination, oxygen is caused to react with ethylene to form ethylene oxide. Concomitant with that reaction is the combustion of ethylene and/or ethylene oxide to carbon dioxide and water (combustion products). Some have theorized that at least a portion of the carbon dioxide is generated by the isomerization of ethylene oxide to acetaldehyde which immediately goes to combustion products.

It is these competing reactions that the workers in the art attempt to affect. Many additives have been used to enhance the reaction. To illustrate this point, it must be recognized that the best procedures employed today to make commercial silver catalysts when used to make a silver only catalyst, i.e., silver impregnated on a porous alpha-alumina support, will result in a catalyst which, under commercial ethylene oxide process conditions (exclusive of gas phase inhibitor addition), generates at best a selectivity or efficiency to ethylene oxide of about 35–50%, and reduced catalytic activity. The most significant contributor to improving selectivity or efficiency and activity is the addition of gas phase organic chloride compounds such as ethyl chloride, ethylene dichloride and vinyl chloride. Many other gas phase additives to enhance selectivity have been depicted in the art (See Law, et al., U.S. Pat. Nos. 2,279,469 and 2,279,470) and they range from the addition of nitrogen oxides, ammonia to xylene. All of them, at one time or another have been found to beneficially affect efficiency.

Another class of additives are those incorporated into the silver catalyst and are not part of the gas phase fed or provided to the catalyst. There are many metals which when added into the silver catalyst beneficially affect the performance of the catalyst. Some say that they act as promoters and others attribute the benefit to an inhibiting or suppressing action. In the absence of the gas phase additives, these metals make little contribution, if any, to the catalyst's performance. However, in the presence of the gas phase additive, the net effect is an improvement in the amount of ethylene oxide produced and a concomitant reduction in carbon dioxide. Such metals cover the spectrum of the Periodic Table and their roles in the reaction are not understood at this time.

Though metals have received much attention, relatively little attention in the literature has been given to the role of anions in this reaction. Silver salts such as silver nitrate, silver lactate and silver oxalate have long been used as a source of silver metal. Since the silver salts are reduced by roasting to the metal form, their selection would appear to have been arbitrary except when those salts deposit or occlude contaminating cations. For example, the manufacture of silver oxalate by the reaction of silver nitrate with potassium oxalate leaves behind in the silver oxalate a small amount of potassium which cannot be removed from the silver oxalate and it goes along for a ride with the silver in the remainder of the catalyst preparation steps.

Some early references in the art have suggested the use of alkali metal halide (see Gould, Sears, Brengle, et al., and Sacken, infra) but they seemed to be more interested in providing a process for adding both alkali, the promoter, and chloride, the inhibitor, to accommodate the known benefits of alkali promotion and chlorine inhibition. See Law, et al., supra. and Evans, infra. By the time of their work, Law, et al., had already proven in commercial operations that gas phase chloride addition was a significant contributor to enhanced production of ethylene oxide. The role of chlorine or chloride was easily speculated about because of silver's known propensity for reaction with chlorine to form silver chloride.

As viewed by the prior art, the role of alkali metal was presumed to provide a promoter component and, with the exception of when the halide form was described for providing halide inhibition, the role of anion has been regarded to be unimportant. One exception is Sacken, U.S. Pat. No. 2,671,764, who describes the benefits derived from the provision of alkali metal sulfates. [This patent will hereinafter be called the "Sacken sulfate" patent to distinguish it from U.S. Pat. No. 2,765,283, in which Sacken employs alkali metal halide additive.] Unquestionably, the Sacken sulfate patent recognizes benefits from the use of alkali metal sulfate as promoters for the silver catalyzed ethylene oxide reaction. However, the Sacken sulfate patent practices the process in the absence of gas phase inhibitor such as organic chlorides. Consequently, the results depicted in the patent is a process which yields a low ethylene oxide selectivity. Even though the Sacken sulfate patent specifies the use of alkali metal sulfate, it is only compared with the corresponding hydroxide in showing that the sulfate anion plays a role in the ethylene oxide reaction. The prime variable in the Sacken sulfate patent appears to be the choice of alkali metal. Other exceptions are U.S. Pat. Nos. 4,414,135 and 4,415,476, in which the first patent proposes the use of cesium bromide or fluoride, and the second patent proposes the use of more than 1000 ppm of sodium and cesium, both as their chlorides (compare U.K. Patent 2,043,481, page 18, Table VI). The last exception is U.S. Pat. No. 4,406,820 which employs certain alkali metal salts of organic acids such as m-hydroxy-benzoic acid and acrylic acid. Such anions would be expected to be converted to combustion products.

DETAILED DESCRIPTION OF PRIOR ART

The manufacture of ethylene oxide by the reaction of oxygen or oxygen-containing gases with ethylene in the presence of a silver catalyst is an old and developed art. For example, U.S. Pat. No. 2,040,782, patented May 12, 1936, describes the manufacture of ethylene oxide by the reaction of oxygen with ethylene in the presence of silver catalysts which contain a class of metal promoters. In U.S. Pat. No. Re. 20,370, dated May 18, 1937, Leforte discloses that the formation of olefin oxides may be effected by causing olefins to combine directly with molecular oxygen in the presence of a silver catalyst. From that point on, the prior art has focused its efforts on improving the catalyst's efficiency in producing ethylene oxide.

In characterizing this invention, the terms "conversion", "selectivity", and "yield" are employed as defined in U.S. Pat. No. 3,420,784, patented Jan. 7, 1969, at column 3, lines 24-35 inclusive. This definition of "selectivity" is consistent with that disclosed in U.S. Pat. No. 2,766,261 at column 6, lines 5-22, and U.S. Pat. No. 3,144,916, lines 58-61. The definitions of "yield" and "conversion" have more varied meaning in the art and are not to be employed as defined, for example, in the aforementioned U.S. Pat. No. 2,766,261. The terms "efficiency" and "selectivity", as used throughout the specification and claims, are intended to be synonymous.

Silver catalysts employed in the manufacture of ethylene oxide have undergone significant changes since their initial period of development. As reported by the art, silver particles were first deposited upon support materials with little attention being paid to support properties, such as surface area, pore volume and chemical inertness. As the art evolved, there developed special technologies related to carriers or supports containing silver that were more effective for the reaction of ethylene with oxygen to produce ethylene oxide. Today, most supports for the silver catalysts are shaped particulate materials which can be loaded in the interior of a reactor wherein the reacting gases and the gaseous products of the reaction are capable of flowing in and about these particulate materials to pass through the reactor and be recovered. The size and shape of the support are variable factors and the particular size and shape selected are peculiar to the reactor employed, the gas flow required, and the pressure drop across the reactor, with other factors also being considered.

The carriers that have been employed are typically made of inorganic materials, generally of a mineral nature. In most cases, the preferred carrier is made of alpha alumina, such as has been described in the patent literature: see for example, U.S. Pat. Nos. 2,294,383; 3,172,893; 3,332,887; 3,423,328; and 3,563,914.

The carriers which are employed for the manufacture of most, if not all, commercially employed ethylene oxide catalysts are produced by companies who do not produce such catalysts. As a rule, the methods of making such carriers are trade secrets of significant value to the carrier manufacturers. Consequently, the catalyst manufacturer cannot know how the carrier is made. Critical to making a carrier which proves uniquely desirable for the manufacture of a successful catalyst can be a number of factors, such as the purity and other physical/chemical properties of raw materials used to make the carrier and the method by which the carrier is made.

The silver that is deposited on these carriers is thought to be in the form of small particles because that is all that can be seen by current microscopic techniques. The patent literature indicates that the size of the silver is a factor in the effectiveness of the catalyst and in most cases fine particle silver is obtained utilizing the standard processes in the art; see, for example, U.S. Pat. Nos. 2,554,459; 2,831,870; 3,423,328 (specifies that silver particles of 150-400 Angstroms are employed); U.S. Pat. No. 3,702,259 (disclosed a preparation procedure for forming silver particles less than 1 micron in diameter) and U.S. Pat. No. 3,758,418 (discloses silver particles having a diameter less than 1000 Angstroms). Improvements in microscopic examinations of silver catalysts enable the observation that the particle size ranges to even smaller values.

The deposition of silver onto the carrier can be achieved by a number of techniques but the two techniques which are most frequently employed involve, in one case, the impregnation of the support with a silver solution followed by heat treatment of the impregnated support to effect deposition of the silver on the support and, in the other case, the coating of the silver on the support by the precipitation of silver or the preformation of silver into a slurry such that the silver particles are deposited on the support and adhere to the support surface when the carrier or support is heated to remove the liquids present. These various procedures are exemplified in various U.S. Patents such as U.S. Pat. Nos. 2,773,844; 3,207,700; 3,501,407; 3,664,970 (see British Patent 754,593) and U.S. Pat. No. 3,172,893.

The surface area provided by the support has been the subject of considerable interest in the development of silver catalysts. Disclosures concerning the surface area of the catalyst carrier can be found in U.S. Pat. No. 2,766,261 (which discloses that a surface area of 0.002-10 $m^2$/gm is suitable); U.S. Pat. No. 3,172,893 which depicts a porosity of 35-65% and a pore diameter of 80-200 microns); U.S. Pat. No. 3,725,307 which depicts a surface area of less than 1 sq.m/gm and an average pore diameter of 10-15 microns); U.S. Pat. No. 3,664,970 (which utilizes a support having a minimum porosity of about 30%, at least 90% of the pores having diameters in the range of 1-30 microns, and the average of such diameters being in the range of 4-10 microns); and U.S. Pat. No. 3,563,914 which utilizes a catalyst support having a surface area of less than 1 sq. m/gm, a volume of 0.23 ml/gm and a particle size between 0.074 and 0.30 mm). Low surface area, inert alpha alumina is favored by the prior art.

It has been known for a long time that impurities present in the catalyst and/or the gas phase can materially impact upon the reaction. In the early development of the art, there were no techniques available for identifying or measuring such impurities. Consequently, one could not isolate the role that such impurities played. However, even in the earliest periods of the development of the art, the use of alkali metals as promoters for the silver catalyzed production of ethylene oxide was extremely well known in the art. U.S. Pat. No. 2,177,361, issued October 1939, has a teaching of the use of alkali metals in silver catalysts. U.S. Pat. No. 2,238,471 discloses that lithium is very desirable as a promoter but that potassium and cesium are detrimental when used in amounts of essentially 10% by weight of potassium hydroxide or cesium hydroxide to the silver oxide employed in making the catalyst. Later, U.S. Pat. No. 2,404,438 states that sodium and lithium are effective promoters for this reaction. Essentially the same teaching can be found in U.S. Pat. No. 2,424,084. U.S. Pat. No. 2,424,086 generalizes about alkali metals as promoters and specifies sodium in particular. In U.S. Pat. No. 2,671,764 (the Sacken sulfate patent), the patentees believe that alkali metals in the form of their sulfates are effective as promoters for such silver catalysts. In particular, the patentees state that sodium, potassium, lithium, rubidium or cesium sulfates may be used as promoters. U.S. Pat. No. 2,765,283 describes the pretreatment of a support with a dilute solution of a chlorine-containing compound and indicates that such chlorine compounds should be inorganic. Particular illustrations cited of suitable inorganic chlorine compounds included sodium chloride, lithium chloride and potassium chlorate. This patent specifies that the amount of the inorganic chlorine-containing compound which is deposited on the catalyst support is from 0.0001% to 0.2% by weight based on the weight of the support. U.S. Pat. No. 2,615,900 to Sears describes the use of metal halide in the treatment of the supported catalyst and specifies that such halides can be of alkali metals such as lithium, sodium, potassium and cesium. The metal halide is present in the range of 0.01% to 50% based upon the weight of metallic silver. The patent also specifies that mixtures of the individual metal halides generally classified in the patent may be used to advantage to enhance the break-in period of a new catalyst composition while at the same time maintaining a moderate but steady activity of the catalyst over an extended period of time during normal operation. Thus, one particular metal halide treated catalyst would provide a short-term high initial activity whereas another of the metal halides would provide a longer term moderate activity for the catalyst. This patent takes the position that the metal halides which are provided in the catalyst serve to inhibit the combustion of ethylene to carbon dioxide and thus classifies these materials as catalyst depressants or anticatalytic materials. U.S. Pat. No. 2,709,173 describes the use of a silver catalyst for making ethylene oxide in which there are provided, simultaneously with the introduction of silver to the solid support, any of the alkali metal halides such as lithium, sodium, potassium, and rubidium compounds of chlorine, bromine and iodine, to enhance the overall production of ethylene oxide. The patent specifies small amounts "of less than about 0.5% are desirable". In particular, the patent emphasizes "proportions of alkali metal halide within the range of about 0.0001 to about 0.1%" are most preferred. The patent states that "although the preferred catalyst composition contains a separate promoter it is not always necessary since during preparation of the catalyst the alkali metal halide may be converted to some extent to the corresponding alkali metal oxide which acts as a promoter." U.S. Pat. No. 2,766,261 appears to draw from the teachings of U.S. Pat. No. 2,238,474 in that cesium and potassium are said to be detrimental in silver catalysts; sodium and lithium are suggested as useful promoters. However, U.S. Pat. No. 2,769,016 finds that sodium, potassium and lithium are promoters when used in the silver catalysts. This latter patent also recommends the pretreatment of the support with dilute solutions of sodium chloride, lithium chloride or potassium chlorate. U.S. Pat. No. 2,799,687 to Gould, et al., states that the addition of metal halides within the range described by Sears in U.S. Pat. No. 2,615,900 is not productive of optimum results. This is said to be especially true in the case of alkali metal halides, particularly the chloride and fluoride of sodium and potassium. The patentees recommend that the inorganic halide component of the catalyst be maintained within the range of 0.01-5 weight percent, preferably 0.01 to 0.1 weight percent, based on the weight of the "silver oxidative catalytic component," i.e., the silver salt transformed into elemental silver. U.S. Pat. No. 3,144,416 mentions a variety of metals as promoters and one of them is cesium. U.S. Pat. No. 3,258,433 indicates that sodium is an effective promoter. U.S. Pat. No. 3,563,913 recommends the use of alkali metals such as lithium compounds as promoters. The preferred amount of promoting material is said to be about 0.03 to 0.5%, by weight of metal oxide based on the weight of the support. U.S. Pat. No. 3,585,217 states that alkali metal chlorides "are known to counteract the formation of carbon dioxide" and "may be incorporated into the catalyst." U.S. Pat. No. 3,125,538 discloses a supported silver catalyst containing a coincidentally-deposited alkali metal selected from among potassium, rubidium and cesium in a specified gram atom ratio relative to silver. The weight of silver is preferably 2-5% by weight of the catalyst. The patentees characterize this catalyst as being especially suitable for the reaction of nitric oxide with propylene. This same catalyst is produced inherently by the processes of the examples of U.S. Pat. No. 3,702,259, as discussed previously, which patent promotes their use for making ethylene oxide. U.S. Pat. Nos. 3,962,136 and 4,012,425 also disclose that same catalyst as being useful for ethylene oxide production. U.S. Pat. No. 3,962,136 describes the coincidental deposition of alkali metal with the silver on the support, the alkali metals being present in their final form on the support in the form of an oxide in which the oxide consists of cesium, rubidium or mixtures of both, optionally combined with a minor amount of an oxide of potassium. The amount of such oxide is from about $4.0 \times 10^{-5}$ gew/kg to about $8.0 \times 10^{-3}$ gew/kg of total catalyst. However, U.S. Pat. No. 4,010,115, patented Mar. 1, 1977, purports to distinguish itself from the other patents by employing as the oxide of the alkali metal the oxide of potassium optionally combined with a minor amount of an oxide of rubidium or cesium. U.S. Pat. No. 4,356,312 describes the use of the same catalyst. Application Ser. No. 317,349, filed Dec. 21, 1972, which is a parent to U.S. Pat. Nos. 3,962,136 and 4,010,115 and others, contains some interesting data deserving of comment. According to example 2 which contains some comparative experiments, there is described the manufacture of a catalyst which contains 310 parts per million by weight of coincidentally-added potassium and that catalyst when employed as an ethylene oxidation catalyst was found to be inactive for the production of ethylene oxide.

U.S. Pat. No. 4,207,210 (corres. Belgium Patent 821,439, based upon British Patent Specification 1,489,335) discloses that a catalyst can be made that is equivalent to that produced in the so-called parent applications cited in U.S. Pat. Nos. 3,962,136, 4,012,425, and 4,010,115 by using a sequential procedure by which the alkali metal is supplied to the support. Thus, the criticality in the method of deposition of alkali metal in the catalyst appears doubtful in the face of that type of disclosure and the disclosure of U.S. Pat. Nos. 4,033,903 and 4,125,480 which describe subjecting used silver-containing catalysts to a post-addition of one or more of potassium, rubidium or cesium. Apparently, such treatment regenerates the catalyst's ability to enhance selectivity to ethylene oxide. Another patent which tends to indicate that a post-addition of alkali metal such as cesium gives results equivalent to either pre-addition or simultaneous addition is U.S. Pat. No. 4,066,575.

German Offenlegungsschrift 2,640,540 discloses in its examples a silver catalyst for ethylene oxide production containing sodium and either potassium, rubidium or cesium.

Japanese Application Publication Disclosure No. 95213/75 is directed to a process for producing ethylene oxide using a catalyst composition comprising silver, barium, potassium and cesium in specified atomic ratios. Table I of this disclosure summarizes the efficiencies achieved with the various catalyst compositions of the examples.

U.S. Pat. No. 4,039,561 discloses a catalyst for preparing ethylene oxide containing silver, tin, antimony, thallium, potassium, cesium and oxygen in specified atomic ratios.

Belgium Patent 854,904 discloses silver catalysts containing various mixtures of sodium and cesium. U.K. Patent Application 2,002,252 discloses, in Table 2, supported silver catalysts containing various mixtures of cesium and thallium, some of which additionally contain potassium or antimony. U.S. Pat. No. 4,007,135 broadly discloses (in column 2, lines 25-30) silver catalysts for alkylene oxide production containing silver "together with a promoting amount of at least one promoter selected from lithium, potassium, sodium, rubidium, cesium, copper, gold, magnesium, zinc cadmium, strontium, calcium, niobium, tantalum, molybdenum, tungsten, chromium, vanadium and barium . . .". U.S. Pat. Nos. 3,844,981 and 3,962,285 disclose catalysts and processes for epoxidizing olefins in the presence of a multimetallic component. The catalyst in the U.S. Pat. No. 3,962,285 patent is said to comprise a minor amount of one or more of palladium, ruthenium, rhenium, iron and platinum with a major amount of silver. The U.S. Pat. No. 3,844,981 patent discloses the preparation of the catalyst from a decomposible salt of group 7b, 1b or the iron group of group 8 of the Periodic Table of the Elements. Preferably, the salt is selected from the group of gold, copper, rhenium, manganese and iron salts. While the patentee contemplates that these metals are in the metallic state, oxidation during epoxidation conditions may occur with one or more of these metals, e.g., rhenium, to form oxyanions containing the metal.

European Patent Publication No. 0003642 discloses, in Table 3, silver-containing catalysts which include mixtures of potassium and cesium, and a catalyst containing sodium and cesium.

Belgium Patent 867,045 discloses supported silver catalysts containing what is referred to as an effective proportion of lithium and a substantially lesser amount of alkali metal selected from among cesium, rubidium and/or potassium.

Belgium Patent 867,185 discloses supported silver catalysts for ethylene oxide production containing a specified amount of potassium and at least one other alkali metal selected from rubidium and cesium.

United Kingdom Patent No. 2,043,481, commonly assigned, describes the use of a synergistic combination of cesium and at least one other alkali metal in combination with silver on an inert support to provide catalysts which were superior to those known to the art at that time. Such catalysts have been widely employed commercially. The alkali metal components are provided to the support by a variety of ways. The alkali metal can be supplied to the support as a salt and many salts of the alkali metals are described. Specific illustration is made of the use of alkali metal sulfates as one of many usable alkali metal compounds.

European Patent Application 85,237 describes an ethylene oxide catalyst wherein the applicants believe they "chemically absorbed" by alcohol wash, cesium and/or rubidium onto the catalyst support, a procedure not unlike that described by Neilsen and Schroer, supra. for potassium treated catalysts.

Japanese patent application Kokai 56/105,750 discloses, among other things, ethylene oxide catalysts containing cesium molybdate or cesium tungstate or cesium borate. The catalyst is stated to have an alumina carrier having a sodium content of less than 0.07 weight % and mainly consisting of alpha-alumina having a specific surface area of 1 to 5 sq. m./gm. The carrier is impregnated with decomposible silver salt solution containing alkali metal boron complex, alkali metal molybdenum complex and/or alkali metal tungsten complex. No examples of mixtures of anions are disclosed. Japanese patent application Kokai 57/21937 discloses thallium-containing catalysts in which the thallium may be borate or titanate salt.

Since the date of filing of the Ser. No. 640,269 patent application, a number of patent documents have been published relating to ethylene epoxidation catalysts which may contain oxyanions. European patent application 247,414, published Dec. 12, 1987, discloses catalysts containing alkali metal and/or barium which may be provided as salts. The salts include nitrates, sulfates, and halides. European patent applications 266,015, published May 4, 1988, and 266,852, published May 11, 1988, disclose catalysts containing a rhenium component, e.g., rhenium oxide, rhenium cation or rhenate or perrhenate anion. An example of a catalyst made from silver oxalate with cesium hydroxide, ammonium perrhenate, and ammonium sulfate is disclosed in the '852 application. Numerous examples of silver catalysts containing cesium, rhenate and co-promoter salts are presented in the '015 application. For instance, Experiment 7-12 reports a catalyst having 13.5 weight percent silver, 338 ppmw (parts per million by weight) cesium (CsOH) 186 ppmw rhenium ($NH_4ReO_4$) and 55 ppmw manganese ($KMnO_4$), experiment 7-6, 12.7 wt %, 421 ppm cesium, 186 ppmw rhenium, 32 ppm sulfur (($NH_4)_2SO_4$); and Experiment 7-26, 14.7 wt % silver, 387 ppmw cesium and 78 ppmw potassium (as sulfate), 186 ppmw rhenium, 32 ppmw sulfur (($NH_4)_2SO_4$), and 184 ppmw tungsten ($H_2WO_4$). Experiments are presented in which vanadate, chlorate, molybdate, chromate, sulfite, phosphate and tungstate anion are added in combination with rhenate anion.

DISCLOSURE OF THE INVENTION

This invention involves the manufacture of impregnated silver catalysts on an inert, preferably alpha-alumina, support (preferably having a size and configuration usable in commercially-operated ethylene oxide tubular reactors) in which there is provided a mixture of cesium salts at least one of which is a cesium salt in which the anions thereof are oxyanions, preferably polyvalent oxyanions, of elements having an atomic number of 21 to 75 and being from groups 3b through 7b, inclusive, of the Periodic Table of the Elements (as published by The Chemical Rubber Company, Cleveland, Ohio, in *CRC Handbook of Chemistry and Physics,* 46th Edition, inside back cover).

The other anion or anions for the cesium may be halide and/or oxyanion of elements other than oxygen therein having an atomic number of either (i) 7 or (ii) 15 to 83 and being from groups 3b to 7b, inclusive, and 3a to 7a, inclusive, of the Periodic Table. Frequently, the catalyst contains at least one anion other than an oxyanion of an element of groups 3b to 7b. The catalyst may contain other alkali and alkaline earth metal components which may be provided in the form of oxides, hydroxides and/or salts. Since cesium-containing components and other alkali and alkaline earth metal components are typically applied as solubilized components in a solvent, intermixing of the charge-satisfying moieties will occur. Hence, a catalyst prepared using cesium sulfate and potassium molybdate will also contain cesium molybdate and potassium sulfate.

The mixture is preferably in an amount sufficient, relative to the amount of silver employed, to yield at STANDARD ETHYLENE OXIDE PROCESS CONDITIONS under oxygen process conditions, as hereinafter defined, a selectivity (or efficiency) of at least 79 percent. An aspect of the invention also involves the process of making ethylene oxide by feeding a gas phase mixture of ethylene, oxygen, recycled $CO_2$ and a gas phase inhibitor to a bed of impregnated silver catalyst of this invention, to produce ethylene oxide. The process for making ethylene oxide is not limited to STANDARD ETHYLENE OXIDE PROCESS CONDITIONS for definition as is the catalyst. Catalysts which have been subjected to process conditions for ethylene oxide manufacture such as STANDARD ETHYLENE OXIDE PROCESS CONDITIONS are considered an important aspect of this invention.

By the use of mixtures of cesium salts, enhanced performance of the catalyst in terms of one or more of activity, efficiency, stability, and sensitivity to changes in process conditions can be obtained, often without resort to other alkali metal or alkaline earth metal additives.

A remarkable aspect of a number of the various embodiments of this invention is the unique insensitivity of these catalysts to gas phase inhibitor addition. The catalysts of this aspect of the invention are remarkably active yet do not require critical doses of gas phase inhibitor for process control. Indeed, many of these catalysts tend to give a rather flat response to gas phase inhibitor addition making their use at commercial practice conditions efficient and free of upsets. Moreover, many of the catalysts exhibit unique high temperature responses yielding high selectivities at high temperatures (e.g., about 270° C.) as are obtained at normal operating temperatures (e.g., about 230°-250° C.). Many of the catalysts of this invention contain a cesium content which according to the prior art would be expected to poison the catalyst's capability for making ethylene oxide.

Many of the catalysts of this invention can employ in their manufacture roasting conditions considerably different from those employed previously. For example, in making the catalysts of this invention, one may use lower temperatures for shorter periods of time to achieve a highly active catalyst at the onset of use in making ethylene oxide.

DETAILED DESCRIPTION OF THE INVENTION

The catalysts of the invention are characterized in their preferred embodiment by a mixture of cesium salts, with or without other alkali metal salts of lithium, sodium, potassium or rubidium or alkaline earth metal salts of magnesium, calcium, strontium or barium, so as to achieve a synergistic result, i.e., an efficiency or activity greater than the greater value obtainable under common conditions from respective catalysts which are the same as said catalyst except that, instead of containing the mixture of anions, each contains only one anion or an improvement in aging characteristics or gas phase inhibitor response by reason of the presence of the amount of one or more of the anions.

As with any catalyst for making ethylene oxide which provides optimum performance, there exists a correlation between (i) the nature of the support;
(ii) the amount of silver on or in the support;
(iii) the components and amounts thereof in addition to the cesium in or on the support;
(iv) the impurities or contaminants provided with the silver or other components; and
(v) the conditions under which the catalyst is used to produce ethylene oxide.

However, in attempting to define any catalyst, there must be a base value from which other factors are determined especially when the factors are variables, each dependent upon the base value for meaning. In the case of this invention, the base value can be the amount of silver or a combination of the amount of silver and the nature of the support. In most cases the latter combination will be the base value. Because at least two values will comprise the base value for catalyst performance, it is apparent that correlations between such combinations and other factors can be quite complex. There is no common thread of logic which integrates all of these combinations and/or factors. To that extent, practice of the invention requires experimental efforts to achieve all or essentially all of the benefits of this invention. Without departing from this script, one skilled in the art can readily achieve the optimum performances of the catalysts of this invention. It should be recognized that such script is commonly followed by the artisan in making any commercially-employable ethylene oxide catalyst. The elements of the script are dependent upon the technology employed in making the catalyst.

The concentration of silver in the finished catalyst may vary from about 2 to 40 or more, often about 2 to 20 or more, weight percent, a commercially preferred range being from about 6% to about 16% by weight of silver. Lower silver concentrations are preferred from a cost per unit catalyst standpoint. However, the optimum silver concentration for any particular catalyst will be dependent upon economic factors as well as performance characteristics, such as catalyst efficiency, rate of catalyst aging and reaction temperature.

The concentration of cesium salt and any other alkali metal and alkaline earth metal salts in the finished catalyst is not narrowly critical and may vary over a wide range. The optimum cesium salt and other salt concentration for a particular catalyst will be dependent upon performance characteristics, such as, catalyst efficiency, rate of catalyst aging and reaction temperature. The concentration of cesium salt in the finished catalyst may vary from about 0.0005 to 1.0 weight percent, preferably from about 0.005 to 0.1 weight percent. Cesium salts alone, or together with at least one other alkali or alkaline earth metal salt, can be employed in the finished catalyst. The ratio of cesium salt to any other alkali metal and alkaline earth metal salt(s), if used, to achieve desired performance is not narrowly critical and may vary over a wide range. The ratio of cesium salt to the other salt(s) may vary from about 0.0001:1 to 10,000:1, preferably from about 0.001:1 to 1,000:1. Preferably, cesium comprises at least about 10, more preferably about 20 to 100, percent (weight) of the total added alkali metal and alkaline earth metal in the finished catalyst.

CARRIER SELECTION

The catalyst carrier employed in practicing the invention may be selected from conventional, porous, refractory materials which are essentially inert to ethylene, ethylene oxide and other reactants and products at reaction conditions. These materials are generally labelled as "macroporous" and consist of porous materials having surface areas less than 10 sq. m/g (square meters per gm of carrier) and preferably less than 1 sq. m/g. The surface area is measured by the conventional B.E.T. method described by Brunauer, S., Emmet, P., and Teller E., in J. Am. Chem. Soc. Vol. 60, pp. 309-16, (1938). They are further characterized by pore volumes ranging from about 0.15-0.8 cc/g, preferably from about 0.2-0.6 cc/q. Pore volumes may be measured by conventional mercury porosimetry or water absorption techniques. Median pore diameters for the above-described carriers range from about 0.01 to 100 microns, a more preferred range being from about 0.5 to 50 microns. The carriers may have monomodal, bimodal or multimodal pore distributions.

For sake of repeatability, in the use and reuse of impregnating solutions the carrier should preferably not contain undue amounts of ions which are exchangeable with the cesium supplied to the catalyst, either in the preparation or use of the catalyst, so as to upset the amount of cesium salts which provides the desired catalyst enhancement. If the carrier contains such ions, the ions should generally be removed by standard chemical techniques such as leaching. However, if the carrier contains an amount of alkali metal, which is transferable to the silver, then either (i) the carrier may be treated to remove such excess alkali metal or alkaline earth metal or (ii) the amount of alkali metal or alkaline earth metal supplied to the catalyst should take into account the transferred alkali metal or alkaline earth metal.

The chemical composition of the carrier is not narrowly critical. Carriers may be composed, for example, of alpha alumina, silicon carbide, silicon dioxide, zirconia, magnesia and various clays. The preferred carriers are alpha-alumina particles often bonded together by a bonding agent and have a very high purity, i.e., at least 98 wt. % alpha-alumina, any remaining components being silica, alkali metal oxides (e.g., sodium oxide) and trace amounts of other metal and non-metal impurities; or they may be of lower purity, i.e., about 80 wt. % alpha-alumina, the balance being a mixture of silicon dioxide, various alkali oxides, alkaline earth oxides, iron oxides, and other metal and non-metal oxides. The carriers are formulated so as to be inert under catalyst preparation and reaction conditions. A wide variety of such carriers are commercially available. Alumina carriers are manufactured by United Catalysts, Inc., Louisville, Ky., and the Norton Company, Akron, Ohio. As stated above, processes for making carriers is often kept a trade secret by the manufacturers. Various alpha-alumina carriers are disclosed, for instance, U.S. Pat. Nos. 3,172,866; 3,908,002; 4,136,063; 4,379,134; 4,368,144; 4,389,338; 4,645,754; and 4,701,437, and European Patent Applications 207,550; 207,541, 224,895; 266,852 and 266,015, and the Peoples Republic of China patent application CN-85-1-02281A.

The carriers may be in the shape of pellets, extruded particles, spheres, rings and the like. The size of the carriers may vary from about 1/16" to $\frac{1}{2}$". The carrier size is chosen to be consistent with the type of reactor employed. In general, sizes in the range of $\frac{1}{8}$" to $\frac{3}{8}$" have been found to be most suitable in the typical fixed bed, tubular reactor used in commercial operations.

As with any supported catalyst, the optimal performance will depend upon optimizing the carrier in terms of its chemical composition (including impurities), surface area, porosity and pore volume. However, the enhancement in performance provided by this invention may be most pronounced when using less than optimized carriers. Thus, in demonstrating the invention in the examples, a variety of carriers are used.

THE ANIONS

The types of anions suitable as counter-ions for the cesium provided in the catalysts of this invention comprise, by way of example only, oxyanions such as sulfate, $SO_4^{-2}$, phosphates, e.g., $PO_4^{-3}$, manganates, e.g., $MnO_4^{-2}$, titanates, e.g., $TiO_3^{-2}$, tantalates, e.g., $Ta_2O_6^{-2}$, molybdates, e.g., $MoO_4^{-2}$, vanadates, e.g., $V_2O_4^{-2}$, chromates, e.g., $CrO_4^{-2}$, zirconates, e.g., $ZrO_3^{-2}$, polyphosphates, nitrates, chlorates, bromates, tungstates, thiosulfates, cerates, and the like. The halide ions include fluoride, chloride, bromide and iodide. It is well recognized that many anions have complex chemistries and may exist in one or more forms, e.g., manganate ($MnO_4^{-2}$) and permanganate ($MnO_4^{-1}$); orthovanadate and metavanadate; and the various molybdate oxyanions such as $MoO_4^{-2}$, $Mo_7O_{24}^{-6}$ and $Mo_2O_7^{-2}$. While an oxyanion, or a precursor to an oxyanion, may be used in solutions impregnating a carrier, it is possible that during the conditions of preparation of the catalyst and/or during use, the particular oxyanion or precursor initially present may be converted to another form which may be an anion in a salt or even an oxide such as a mixed oxide with other metals present in the catalyst. In many instances, analytical techniques may not be sufficient to precisely identify the species present. The invention is not intended to be limited by the exact species that may ultimately exist on the catalyst during use but rather reference herein to oxyanions is intended to provide guidance to understanding and practicing the invention.

The mixture of cesium salts comprises at least one cesium salt of an oxyanion of an element having an atomic number of 21 to 75 and being from groups 3b to 7b, inclusive, of the Periodic Table. Preferably, the cesium salts comprise (a) at least one of cesium molybdate, cesium rhenate, cesium manganate, cesium tungstate, and cesium titanate with (b) at least one other cesium salt not in set (a). Often the cesium salts of set (b) comprise halide, sulfate, vanadate, chromate, tantalate, zirconate, and phosphate.

The ratio of cesium salts may vary widely. Generally, however, at least one cesium salt will comprise at least 20 mole percent of the total cesium salts. In the preferred embodiments, the salts of set (a) will comprise at least about 30, often at least about 50, say, about 50 to 90 or 95, mole percent of the total cesium salts. In some instances, it has been found beneficial to add more anion than is required to associate with the total alkali metal and alkaline earth metal being provided to the catalyst. The reason why such additional anion is beneficial in these situations is not known. The additional anion may be added in the form of an acid, an ammonia salt, an amine salt, etc., or a portion of the alkali metal and/or alkaline earth metal may be added as an acid salt, e.g., cesium hydrogen sulfate.

CATALYST PREPARATION

A variety of procedures may be employed for preparing catalysts containing the aforementioned mixture of cesium salts, alone or with one or more other alkali metal salts (excluding francium salts) and/or alkaline earth metal salts in accordance with the present invention. The preferred procedure comprises: (1) impregnating a porous catalyst carrier with a solution comprising a solvent or solubilizing agent, silver complex in an amount sufficient to deposit the desired weight of silver upon the carrier, and the aforementioned salts of cesium, either alone or with other alkali metal and/or alkaline earth metal salt and (2) thereafter treating the impregnated support to convert the silver salt to silver metal and effect deposition of silver, and the cesium and any other alkali and alkaline earth metal salts on the exterior and interior surfaces of the support. Silver and alkali and alkaline earth metal salt depositions are generally accomplished by heating the carrier at elevated temperatures to evaporate the liquid within the support and effect deposition of the silver and alkali and alkaline earth metal salt onto the interior and exterior carrier surfaces. Impregnation of the carrier is the preferred technique for silver deposition because it utilizes silver more efficiently than coating procedures, the latter being generally unable to effect substantial silver deposition onto the interior surface of the carrier. In addition, coated catalysts are more susceptible to silver loss by mechanical abrasion.

The sequence of impregnating or depositing the surfaces of the carrier with silver and alkali and alkaline earth metal salts is optional. Thus, impregnation and deposition of silver and salts may be effected coincidentally or sequentially, i.e., the salts may be deposited prior to, during, or subsequent to silver addition to the carrier. The alkali and alkaline earth metal salts may be deposited together or sequentially. For example, one or more of the cesium salts may be deposited first followed by the coincidental or sequential deposition of silver and the other alkali and alkaline earth metal salts, or such other alkali or alkaline earth metal salts may be deposited first followed by coincidental or sequential deposition of silver and at least one cesium salt.

Impregnation of the catalyst carrier is effected using one or more solutions containing silver and alkali metal and alkaline earth metal salts in accordance with well-known procedures for coincidental or sequential depositions. For coincidental deposition, following impregnation the impregnated carrier is heat or chemically treated to reduce the silver compound to silver metal and deposit the salts onto the catalyst surfaces.

For sequential deposition, the carrier is initially impregnated with silver or alkali metal or alkaline earth metal salt (depending upon the sequence employed) and then heat or chemically treated as described above. This is followed by a second impregnation step and a corresponding heat or chemical treatment to produce the finished catalyst containing silver and salts.

In making the catalysts of this invention, the alkali metal and alkaline earth metal salts have such high melting temperatures that when deposited on the support with silver compound, and subjected to heating to convert the silver compound to silver metal, the salts preferably remain essentially unchanged. Of course, it is realized that alkali metal and alkaline earth metal salts having an unstable oxidation state will change to a stable oxidation state or states, e.g., sulfites to sulfates. Alkali metal and alkaline earth metal salts used in this invention having a stable oxidation state will remain essentially unchanged. This is contrary to what occurs when the alkali metal or alkaline earth metal is deposited as the hydroxide or carbonate both of which may transform to different salt form (e.g. nitrate) during the heating (roasting) step depending on the roast conditions.

The silver solution used to impregnate the carrier is comprised of a silver compound in a solvent or complexing/solubilizing agent such as the silver solutions disclosed in the art. The particular silver compound employed may be chosen, for example, from among silver complexes, nitrate, silver oxide or silver carboxylates, such as, silver acetate, oxalate, citrate, phthalate, lactate, propionate, butyrate and higher fatty acid salts. Desirably, silver oxide complexed with amines is the preferred form of silver in the practice of the invention.

A wide variety of solvents or complexing/solubilizing agents may be employed to solubilize silver to the desired concentration in the impregnating medium. Among those disclosed in the art as being suitable for this purpose are lactic acid (U.S. Pat. No. 2,477,436 to Aries; and U.S. Pat. No. 3,501,417 to DeMaio); ammonia (U.S. Pat. No. 2,463,228 to West, et al.); alcohols, such as ethylene glycol (U.S. Pat. No. 2,825,701 to Endler, et al.,; and U.S. Pat. No. 3,563,914 to Wattimina); and amines and aqueous mixtures of amines (U.S. Pat. No. 2,459,896 to Schwarz; U.S. Pat. No. 3,563,914 to Wattimina; U.S. Pat. No. 3,215,750 to Benisi; U.S. Pat. No. 3,702,259 to Nielsen; and U.S. Pat. Nos. 4,097,414, 4,374,260 and 4,321,206 to Cavitt).

Following impregnation of the catalyst carrier with silver and alkali metal and alkaline earth metal salts, the impregnated carrier particles are separated from any remaining non-absorbed solution. This is conveniently accomplished by draining the excess impregnating medium or, alternatively, by using separation techniques, such as, filtration or centrifugation. The impregnated carrier is then generally heat treated (e.g., roasted) to effect decomposition and reduction of the silver metal compound (complexes in most cases) to metallic silver and the deposition of alkali metal and alkaline earth metal salts. Such roasting may be carried out at a temperature of from about 100° C. to 900° C., preferably from 200° to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support (e.g., U.S. Pat. No. 3,563,914 suggests heating for less than 300 seconds to dry, but not roast to reduce, the catalyst; U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range), it is only important that the reduction time be correlated with temperature such that substantially complete reduction of the silver salt to metal is accomplished. A continuous or step-wise heating program is desirably used for this purpose. Continuous roasting of the catalyst for a short period of time, such as for not longer than ½ hour is preferred and can be effectively done in making the catalysts of this invention. A special attribute of the catalysts of this invention is that they are more amenable to roasting at lower temperatures, such as lower than about 500° C., than the catalysts of U.K. Patent 2,043,481, without the sacrifice of performance characteristics.

Heat treatment is preferably carried out in air, but a nitrogen or carbon dioxide atmosphere may also be employed. The equipment used for such heat treatment may use a static or flowing atmosphere of such gases to effect reduction, but a flowing atmosphere is much preferred.

An important consideration in making the catalyst of this invention is to avoid the use of strongly acidic or basic solutions which can attack the support and deposit impurities which can adversely affect the performance of the catalyst. The preferred impregnation procedure of U.K. Patent 2,043,481 coupled with the high roasting temperature, short residence time procedure which the patent also described is especially beneficial in minimizing such catalyst contamination. However, the use of the salts of this invention coupled with the high purity supports allows one to use lower temperatures though short residence times are preferred.

The particle size of silver metal deposited upon the carrier is asserted by a portion of the prior art to be a function of the catalyst preparation procedure employed. This may seem to be the case because of the limited ability of the art to effectively view the surface of the catalyst. Thus the space between the silver particles seen on the carrier has not been characterized sufficiently to say whether only such particles of silver represent the silver on the carrier. However, the particular choice of solvent and/or complexing agent, silver compound, heat treatment conditions and catalyst carrier may affect, to varying degrees, the range of the size of the resulting silver particles seen on the carrier. For carriers of general interest for the production of ethylene oxide, a distribution of silver particle sizes in the range of 0.005 to 2.0 microns is typically obtained. However, the role of particle size of the silver catalyst upon the effectiveness of the catalyst in making ethylene oxide is not clearly understood. In view of the fact that the silver particles are known to migrate on the surface of the catalyst when used in the catalytic reaction resulting in a marked change in their size and shape while the catalyst is still highly effective suggests that the silver particle size viewed on the support surfaces of the catalyst may not be a significant factor in catalytic performance.

ETHYLENE OXIDE PRODUCTION

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as, temperature, pressure, residence time, concentration of reactants, gas phase diluents (e.g., nitrogen, methane and $CO_2$), gas phase inhibitors (e.g., ethyl chloride and ethylene dichloride), and the like. The gases fed to the reactor may contain modifiers or inhibitors or additives such as disclosed by Law, et al., in U.S. Pat. Nos. 2,279,469 and 2,279,470, such as nitrogen oxides and nitrogen oxides generating compounds. See also, European Patent No. 3642. In addition, the desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the commercially-practiced processes are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large-scale reactors are generally on the order of about 0.1-5 seconds. Oxygen may be supplied to the reaction in an oxygen-containing stream, such as air or as commercial oxygen. The resulting ethylene products using conventional methods. However, for this invention, the ethylene oxide process envisions the normal gas recycle encompassing carbon dioxide recycle in the normal concentrations.

STANDARD ETHYLENE OXIDE PROCESS CONDITIONS

The STANDARD ETHYLENE OXIDE PROCESS CONDITIONS (ABBR. "CONDITIONS") for characterizing the catalysts of this invention involves the use of a standard backmixed autoclave with full gas recycle including carbon dioxide. The CONDITIONS may be operated with some variation in ethylene, oxygen and gas phase inhibitor feed. Two cases are illustrated: *air process conditions,* which simulates in the backmixed reactor the typical conditions employed in commercial air-type ethylene oxide processes where air is used to supply the molecular oxygen and the *oxygen process conditions,* which simulates in the backmixed reactor the typical conditions in commercial oxygen-type ethylene oxide processes where molecular oxygen, as such, is employed. Each case provides a different efficiency but it is the rule for practically all cases that air as the oxygen feed, using lower amounts of oxygen and ethylene will yield an efficiency to ethylene oxide which is about 2 to 4 percentage points lower than that when molecular oxygen is employed as oxygen feed. The CONDITIONS employ the well known backmixed, bottom-agitated "Magnedrive" autoclaves described in Figure 2 of the paper by J. M. Berty entitled "Reactor for Vapor Phase-Catalytic Studies", in *Chemical Engineering Progress,* Vol. 70, No. 5, pages 78-84, 1974. The CONDITIONS employ 1.0 mole % ethylene oxide in the outlet gas of the reactor under the following standard inlet conditions:

| Component | Air process Conditions, Mole % | Oxygen process Conditions, Mole % |
|---|---|---|
| Oxygen | 6.0 | 8.0 |
| Ethylene | 8.0 | 30 |
| Ethane | 0.5 | 0.5 |
| Carbon Dioxide | 6.5 | 6.5 |
| Nitrogen | Balance of Gas | Balance of Gas |
| Parts per million ethyl chloride (or one-half such amount when ethylene dichloride is used) | 7.5 | 10 |

The pressure is maintained constant at 275 psig and the total outlet flow is maintained at 22.6 SCFH. SCFH refers to cubic feet per hour at standard temperature and pressure, namely, 0° C. and one atmosphere. The outlet ethylene oxide concentration is maintained at 1.0% by adjusting the reaction temperature. Thus, temperature (° C.) and catalyst efficiency are obtained as the responses describing the catalyst performance.

The catalyst test procedure used in the CONDITIONS involves the following steps:

1. 80 cc of catalyst is charged to the backmixed autoclave. The volume of catalyst is measured in a 1 inch I.D. graduated cylinder after tapping the cylinder several times to thoroughly pack the catalyst. The volume of catalyst is alternatively calculated from the packing density of the carrier and the amount of silver and additives. The weight of the catalyst is noted.

2. The backmixed autoclave is heated to about reaction temperature in a nitrogen flow of 20 SCFH with the fan operating at 1500 rpm. The nitrogen flow is then discontinued and the above-described feed stream is introduced into the reactor. The total gas outlet flow is adjusted to 22.6 SCFH. The temperature is adjusted over the next few hours so that the ethylene oxide concentration in the outlet gas is approximately 1.0%.

3. The outlet oxide concentration is monitored over the next 4–6 days to make certain that the catalyst has reached its peak steady state performance. The temperature is periodically adjusted to achieve 1% outlet oxide. The selectivity of the catalyst to ethylene oxide and the temperature are thus obtained.

The standard deviation of a single test result reporting catalyst efficiency in accordance with the procedure described above is 0.7% efficiency units. The running of a multiplicity of tests will reduce the standard deviation by the square root of the number of tests.

The specific STANDARD ETHYLENE OXIDE PROCESS CONDITIONS are used in the examples below unless indicated otherwise. In commercial processes, typical operating conditions can vary and the amounts of the ingredients employed can be adjusted to achieve the best efficiencies. In particular the amounts of ethane, carbon dioxide and organic chloride can be varied to optimize efficiency for the manufacture of ethylene oxide. Ethane is an impurity contained in varying amounts in ethylene raw material. Ethane can also be added to a commercial reactor to provide better control of the chloride's inhibitor action. Typically, the amount of ethane used in commercial processes can vary from about 0.001 to about 5 mole percent for achieving optimization under both air process conditions and oxygen process conditions. As the concentration of ethane increases in the reactor, the effective surface chloride concentration on the catalyst is believed to be decreased thereby decreasing the ability of chloride to promote/inhibit reactions that increase efficiency for the manufacture of ethylene oxide. The amount of chloride, e.g., ethyl chloride or ethylene dichloride, can be varied to provide the needed promoter/inhibitor action commensurate with the ethane levels encountered in a particular process and the type of alkali metal and alkaline earth metal salts used in the catalyst. The amount of organic chloride used in commercial processes can typically vary from about 1.0 ppm to about 100 ppm for achieving optimization under both air process conditions and oxygen process conditions. Carbon dioxide is generally considered an inhibitor, and the inhibitor effect of carbon dioxide on process efficiency may be variable with its concentration. With different types of alkali metal and alkaline earth metal salts used in preparation of the catalysts of this invention, different concentrations of carbon dioxide may be more desirable in certain commercial processes. Typically, the amount of carbon dioxide used in commercial processes can vary from about 2 to about 15 mole percent for achieving optimization under both air process conditions and oxygen process conditions. The amount of carbon dioxide is dependent on the size and type of carbon dioxide scrubbing system employed. The optimization of the amounts of ethane, carbon dioxide and organic chloride provides catalysts which are especially suitable for obtaining desired efficiencies in commercial ethylene oxide manufacture. Catalysts which have been subjected to process conditions for ethylene oxide manufacture such as STANDARD ETHYLENE OXIDE PROCESS CONDITIONS are considered an important aspect of this invention.

The following detailed procedures are provided as illustrative of methods and carriers which are useful for preparing catalysts according to the invention. These examples are by way of illustration only and are not to be construed as limiting the scope of the invention described herein.

Typical alpha-alumina carriers useful in practicing this invention are the following:

CARRIER "A"

Chemical Composition of Carrier "A"

alpha Alumina—98.57 wt. %

| Impurities (in bulk): | |
|---|---|
| $SiO_2$ | .99 wt. % |
| CaO | .008 wt. % |
| $Na_2O$ | .226 wt. % |
| $Fe_2O_3$ | .034 wt. % |
| $K_2O$ | .075 wt. % |
| Physical Properties of Carrier "A" | |
| Surface Area (1) | 0.36–0.55 m²/g typically between 0.40 and 0.50 m²/g |
| Pore Volume (2) (or water absorption) | 0.52 cc/g |
| Packing Density (3) | 0.71 g/ml |
| Median Pore diameter (4) | 20–30 microns |
| Pore Size Distribution, % Total Pore Volume (4) | |

| Pore Size, Microns | % Total Pore Volume |
|---|---|
| <0.1 | 0.0 |
| 0.1–1.0 | About 6.0 |
| 1.0–10.0 | 37.0 |
| 10.0–30.0 | 16.0 |
| 30.0–100 | 32.0 |
| >100 | 9.0 |

CARRIER "B"

Chemical Composition of Carrier "B"

alpha-Alumina—about 99.5+ wt. %

Acid Leachable Impurities

Leachate contained 5 ppm $SO_4^{-2}$, 18 ppm $Na^+$, 1.4 ppm $Li^+$, 1 ppm $Cl^-$, 2 ppm $NO_3$

| Physical Properties of Carrier "B" | |
|---|---|
| Surface Area (1) | 0.43 m²/g |
| Pore Volume (2) | 0.44 cc/g |
| Packing Density (3) | 0.705 g/cc |

| -continued | |
|---|---|
| Median Pore Diameter (4) | 10.2 microns |
| Pore size Distribution, % Total Pore Volume (4) | |
| Pore Size, Microns | % Total Pore Volume |
| <0.1 | 0 |
| 0.1–1.0 | 0 |
| 1–10 | 51.4 |
| 10–30 | 4.6 |
| 30–100 | 21.0 |
| >100 | 23.0 |

CARRIER "C"

Chemical Composition of Carrier "C"

alpha-Alumina—99.84 wt. %

| Impurities (in bulk) | |
|---|---|
| $Na_2O$ | 0.02 wt. % |
| $K_2O$ | 0.01 wt. % |
| $SiO_2$ | 0.01 wt. % |
| Oxides of Ca and Mg | 0.03 wt. % |

Acid Leachable Impurities

Leachate contained 80 ppm $Na^+$, 17 ppm $K^+$.

| Physical Properties of Carrier "C" | |
|---|---|
| Surface Area (1) | 0.436 $m^2$/g |
| Pore Volume (2) | 0.502 cc/g |
| Packing Density (3) | 0.696 g/cc |
| Median Pore Diameter (4) | 20.0 microns |
| Apparent Porosity (%) | 66.3 |
| % Water Absorption | 50.0 |
| Attrition Loss/Hr. (%) | 23.2 |
| 25 Foot Drop Test (% Passing) | 97 |
| Crush Strength Average, lbs. | 14.9 |
| Pore Size Distribution, % Total Pore Volume (4) | |
| Pore Size Microns | % Total Pore Volume |
| $P_1$ (less than 0.1) | 0 |
| $P_2$ (0.1–0.5) | 2.0 |
| $P_3$ (0.5–1.0) | 5.5 |
| $P_4$ (1.0–10.0) | 35.0 |
| $P_5$ (10.0–100) | 53.0 |
| $P_6$ (greater than 100) | 4.5 |

CARRIER "D"

Chemical Composition of Carrier "D"

Alpha-Alumina—about 99.5+ wt. %

Acid Leachable Impurities

Leachate contained 4 ppm $Na^+$, less than 0.01 ppm $K^+$, less than 0.01 ppm $Ca^{++}$, less than 0.01 ppm $Mg^{++}$.

| Physical Properties of Carrier "D" | |
|---|---|
| Surface Area (1) | 0.487 $m^2$/g |
| Pore Volume (2) | 0.429 cc/g |
| Packing Density (3) | 41.64 lbs/$ft^3$ |
| Median Pore Diameter (4) | 47 microns |
| Apparent Porosity | 65% |
| % Water Absorption | 48.9 |
| Crush Strength Average, lbs. | 9.0 |
| Pore Size Distribution, % Total Pore Volume | |
| Pore Size Microns | % Total Pore Volume |
| $P_1$ (<0.1) | 0.0 |
| $P_2$ (0.1–0.5) | 2.0 |

| -continued | |
|---|---|
| $P_3$ (0.5–1.0) | 7.0 |
| $P_4$ (1.0–10) | 30.0 |
| $P_5$ (10–100) | 26.0 |
| $P_6$ (>100) | 35.0 |

CARRIER "E"

Carrier E is an alpha-alumina carrier prepared by calcining to a maximum temperature of about 1025° C., gamma-alumina (available as N-6573 from the Norton Company, Akron, Ohio) in the presence of about 3.55 weight percent ammonium fluoride as fluxing agent. The carrier contains at least 99.0 weight percent alpha alumina, about 0.2 weight percent fluoride and as water leachable components:

| aluminum | 132 ppmw |
|---|---|
| calcium | 50 ppmw |
| magnesium | 5 ppmw |
| sodium | 66 ppmw |
| potassium | 14 ppmw |
| fluoride | 425 ppmw |
| nitrate | 1 ppmw |
| phosphate | 11 ppmw |
| fluorophosphate | 2 ppmw |
| sulfate | 6 ppmw |
| silicon | 10 ppmw |
| Physical Properties of Carrier "E" | |
| Surface Area (1) | 1.17 $m^2$/g |
| Pore Volume (2) | 0.68 cc/g |
| Median Pore Diameter (3) | 1.8 microns |
| Packing Density (4) | 0.53 g/ml. |
| Pore Size Distribution, % Total Pore Volume | |
| Pore Size Microns | % Total Pore Volume |
| $P_1$ (<0.1) | 0 |
| $P_2$ (0.1–0.5) | 2 |
| $P_3$ (0.5–1.0) | 9.5 |
| $P_4$ (1.0–10) | 84.5 |
| $P_5$ (10–100) | 1 |
| $P_6$ (>100) | 3 |

Carrier "F"

Carrier F is an alpha-alumina carrier prepared by calcining to a maximum temperature of about 1100° C., gamma-alumina (N-6573) which had been impregnated with an aqueous 1M ammonium fluoride solution. The carrier contains at least 99.0 weight percent alpha-alumina and about 0.2 weight percent fluoride and has a surface area of 1.1 square meters per gram, a pore volume of 0.76 cubic centimeters per gram and a packing density of about 0.52 grams per milliliter.

CARRIER "G"

Carrier G is an alpha-alumina carrier prepared by calcining to a maximum temperature of about 1100° C., gamma-alumina (N-6573) which had been impregnated with aqueous 1M ammonium fluoride solution. The carrier contains at least 99.0 weight percent alpha-alumina and about 0.25 weight percent fluoride and has a surface area of 1.0 square meter per gram, a pore volume of 0.756 cubic centimeters per gram and a packing density of 0.52 grams per milliliter.

CARRIER "H"

Carrier H is an alpha-alumina carrier prepared by calcining to a maximum temperature of about 1100° C., gamma-alumina (available as N-7759 from the Norton Company) which had been impregnated with aqueous 1M ammonium fluoride solution. The carrier contains at least 99.0 weight percent alpha-alumina and about 0.62 weight percent fluoride and has a surface area of 1.0 square meter per gram, a pore volume of 0.74 cubic centimeters per gram and a packing density of 0.49 grams per milliliter.

CARRIER "I"

Carrier I is a high purity (99.3%), alpha alumina support containing as acid leachable components (Inductively Coupled Plasma Spectroscopy):

| Element | PPM (Weight) |
|---|---|
| Ag | 0.2 |
| Al | 164 |
| B | 0.2 |
| Ba | 0.3 |
| Ca | 83 |
| Cd | less than 0.1 |
| Co | less than 0.1 |
| Cr | less than 0.1 |
| Cu | less than 0.1 |
| Fe | 2 |
| Mg | 6 |
| Na | 130 |
| Pb | 0.5 |
| Sb | 0.7 |
| Si | 104 |
| Sn | 0.7 |
| Ti | 7 |
| V | 7 |
| Zn | 0.2 |

The carrier has an average pore diameter of 0.54 micron, a pore volume of about 0.31 cc/g, and a surface area of about 0.8 square meters per gram.

CARRIER "J"

Carrier J is an alpha-alumina carrier prepared by calcining gamma-alumina (N-6573) to a maximum temperature of about 1025° C. which had been impregnated with an aqueous 3.44 weight percent ammonium fluoride solution. The carrier contains at least 99.0 weight percent alpha-alumina, about 0.2 weight percent fluoride and as water leachable components:

| | |
|---|---|
| aluminum | 118 ppmw |
| calcium | 68 ppmw |
| magnesium | 7 ppmw |
| potassium | 3 ppmw |
| sodium | 36 ppmw |
| fluoride | 375 ppmw |
| nitrate | 4 ppmw |
| phosphate | 30 ppmw |
| fluorophosphate | 3 ppmw |
| sulfate | 2 ppmw |
| silicon | 6 ppmw |
| Physical Properties of Carrier "J" | |
| Surface Area | 1.09 m²/g |
| Pore Volume | 0.668 cc/g |
| Median Pore Diameter | 1.85 microns |
| Packing Density | 0.53 g/ml |
| Pore Size Distribution, % Total Pore Volume | |
| Pore Size Microns | % Total Pore Volume |
| $P_1$ (<0.1) | 0 |
| $P_2$ (0.1–0.5) | 1 |
| $P_3$ (0.5–1.0) | 6 |
| $P_4$ (1.0–10) | 88.5 |
| $P_5$ (10–100) | 1.5 |
| $P_6$ (>100) | 3 |

CARRIER "K"

Carrier K is Carrier J which had been washed five times with hot deionized water (approximately 70° C.).

CARRIER "L"

Carrier L is Carrier K which had been calcined at 900° C. for 1 hour.

CARRIER "M"

Carrier "M" is an alpha-alumina carrier prepared by calcining to a maximum temperature of about 1025° C. gamma-alumina (N-6573) in the presence of about 3.5 weight percent fluoride using ammonium fluoride as fluxing agent. The carrier contains at least 99.0 weight percent alpha-alumina, about 0.2 weight percent fluoride and as water leachable components:

| | |
|---|---|
| aluminum | 98 ppmw |
| calcium | 35 ppmw |
| magnesium | 8 ppmw |
| sodium | 30 ppmw |
| potassium | 5 ppmw |
| fluoride | 285 ppmw |
| phosphate | 5 ppmw |
| fluorophosphate | 3 ppmw |
| sulfate | 1 ppmw |
| silicon | 3 ppmw |
| Physical Properties of Carrier "M" | |
| Surface Area | 0.96 m²/g |
| Pore Volume | 0.70 cc/g |
| Median Pore Diameter | 2.3 microns |
| Packing Density | 0.52 g/ml |
| Pore Size Distribution, % Total Pore Volume (4) | |
| Pore Size Microns | % Total Pore Volume |
| $P_1$ (<0.1) | 0 |
| $P_2$ (0.1–0.5) | 1 |
| $P_3$ (0.5–1.0) | 4 |
| $P_4$ (1.0–10) | 88 |
| $P_5$ (10–100) | 2 |
| $P_6$ (>100) | 5 |

CARRIER "N"

Carrier "N" is an alpha-alumina carrier prepared by calcining to a maximum temperature of about 1025° C. gamma-alumina (N-6573) in the presence of about 4.06 weight percent fluoride using ammonium fluoride as fluxing agent. The carrier contains at least 99.0 weight percent alpha-alumina, about 0.2 weight percent fluoride and as water leachable components:

| | |
|---|---|
| aluminum | 110 ppmw |
| calcium | 79 ppmw |
| magnesium | 9 ppmw |
| sodium | 26 ppmw |
| potassium | 5 ppmw |
| fluoride | 330 ppmw |
| phosphate | 7 ppmw |
| fluorophosphate | 4 ppmw |
| sulfate | 6 ppmw |
| silicon | 5 ppmw |
| Physical Properties of Carrier "N" | |
| Surface Area | 0.93 m²/g |
| Pore Volume | 0.72 cc/g |
| Median Pore Diameter | 2.3 microns |
| Packing Density | 0.53 g/ml |
| Pore Size Distribution, % Total Pore Volume (4) | |
| Pore Size Microns | % Total Pore Volume |
| $P_1$ (<0.1) | 0 |
| $P_2$ (0.1–0.5) | 1 |

-continued

| | |
|---|---|
| P₃ (0.5–1.0) | 3 |
| P₄ (1.0–10) | 89 |
| P₅ (10–100) | 2 |
| P₆ (>100) | 5 |

(1) Method of measurement described in "Adsorption Surface Area and Porosity", S. J. Gregg and K. S. W. Sing, Academic Press (1967), pages 316–321.
(2) Method of measurement as described in ASTM C20–46.
(3) Calculated value based on conventional measurement of the weight of the carrier in a known volume container.
(4) Method of measurement described in "Application of Mercury Penetration to Materials Analysis", C. Orr Jr., Powder Technology, Vol.3, pp. 117–123 (1970).

Attrition Loss and Crush Strength Average and Range were determined according to Test No. 45 and Test No. 6, respectively, as referred to in *Catalyst Carriers*, Norton Company, Akron, Ohio Bulletin CC-11, 1974. 25 foot Drop Test was determined by dropping carrier pills through a tube for a vertical distance of 25 feet onto a steel plate and observing for breakage. Non-breakage of carrier pills indicated percent passing. Acid Leachable Impurities were determined by contacting carrier pills with 10% nitric acid for one hour and determining extracted cations by standard Atomic Absorption spectroscopy techniques Inductively Couples Spectroscopy techniques may also be used for such determinations.

CATALYST PREPARATION TECHNIQUES

The carrier, as indicated, was impregnated under vacuum as hereinafter described with a solution of silver complex and alkali metal and alkaline earth metal salts. The alkali metal and/or alkaline earth metal-containing components need not be introduced as the salts. For instance, cesium hydroxide may be used in conjunction with an ammonium salt (e.g, ammonium sulfate) or acid (e.g., sulfuric acid) or organic compound (e.g., ethylsulfonate) and under conditions of catalyst preparation or use, conversion is made to the desired species. The impregnating solution was prepared at a concentration such that the finished catalyst contained the desired amounts of silver, cesium salt and/or the other alkali metal salts. The required concentration of silver and alkali metal salts in solution for the given carrier is calculated from the packing density (grams/cc) and pore volume of the carrier which are either known or readily determined. Assuming that all of the silver in the impregnating solution contained in the pores of the carrier is deposited upon the carrier, approximately 21 wt. % silver in solution is necessary to prepare a catalyst containing about 11 wt. % silver on the catalyst. The relationship can vary depending upon the nature of the carrier, e.g., pore volume may influence the amount of silver deposited from a given solution. The required concentration of alkali metal salts in solution is obtained by dividing the solution silver concentration by the ratio of silver to alkali metal salts desired in the finished catalyst. Thus, to obtain 11.0 wt. % Ag and 0.0047 wt. % Cs, the ratio is approximately 2330 and the required cesium concentration in solution is 0.009 wt. %. The solution containing the desired concentrations of silver and alkali metal salts was prepared as described below.

IMPREGNATING SOLUTION PREPARATION

The indicated amounts of ethylenediamine (high purity grade) were mixed with indicated amounts of distilled water. Then oxalic acid dihydrate (reagent grade) was then added slowly to the solution at ambient temperature (23° C.) while continuously stirring. During this addition of oxalic acid, the solution temperature rose to about 40° C. due to the reaction exotherm. Silver oxide powder (Metz Corporation) was then added to the diamine-oxalic acid salt water solution while maintaining the solution temperature below about 40° C. Finally, monoethanolamine, aqueous alkali metal salt solution(s) and distilled water were added to complete the solution. The specific gravity of the resulting solution was about 1.3–1.4 g/ml.

CATALYST PREPARATION

Carrier was impregnated in a 12 inches long by 2 inches I.D. glass cylindrical vessel equipped with a suitable stopcock for draining the carrier after impregnation. A suitable size separatory funnel for containing the impregnating solution was inserted through a rubber stopper equipped with a metal tube for attaching a vacuum line into the top of the impregnating vessel. The impregnating vessel containing the carrier was evacuated to approximately 2 inches of mercury pressure for about 20 minutes after which the impregnating solution was slowly added to the carrier by opening the stopcock between the separatory funnel and the impregnating vessel until the carrier was completely immersed in solution, the pressure within the vessel being maintained at approximately 2 inches of mercury. Following addition of the solution, the vessel was opened to the atmosphere to attain atmospheric pressure, the carrier then remained immersed in the impregnating solution at ambient conditions for about 1 hour, and thereafter drained of excess solution for about 30 minutes. The impregnated carrier was then heat treated as follows (unless stated otherwise) to effect reduction of silver salt and deposition of alkali metal salts on the surface. The impregnated carrier was spread out in a single layer on a 2⅜ inches wide endless stainless steel belt (spiral weave) and transported through a 2 inches by 2 inches square heating zone for 2.5 minutes, the heating zone being maintained at 500° C. by passing hot air upward through the belt and about the catalyst particles at the rate of 266 SCFH. The hot air was generated by passing it through a 5 ft. long by 2 inches I.D. stainless steel pipe which was externally heated by an electric furnace (Lindberg ™ tubular furnace: 2½ inches I.D., 3 feet long heating zone) capable of delivering 5400 watts. The heated air in the pipe was discharged from a square 2 inches by 2 inches discharge port located immediately beneath the moving belt carrying the catalyst carrier. After being roasted in the heating zone, the finished catalyst was weighed, and based upon the weight gain of the carrier, and the known ratios of silver to alkali metal salt in the impregnating solution, it was calculated to contain the wt. % of silver, and wt. % alkali metal salts indicated.

The analysis for silver was carried out by the following method: An approximately 50 g sample of catalyst was powdered in a mill and 10 g of the powdered sample weighed to the nearest 0.1 mg. The silver in the catalyst sample was dissolved in hot (80° C.) 50%, by volume, nitric acid solution. The insoluble alumina particles were filtered and washed with distilled water to remove all adhering nitrate salts of Ag, Cs, etc. This solution was made up to 250 ml in a volumetric flask using distilled water. A 25 ml aliquot of this solution was titrated according to standard procedures using a 0.1 Normal solution of ammonium thiocyanate and ferric nitrate as indicator. The amount of Ag so determined in 250 ml solution was then used to calculate the weight percent silver in the catalyst sample.

Silver and alkali metal concentrations for all catalysts described in the specification are calculated values as described above.

Carriers are nominally ring shape having dimensions of about ⅛×5/16×5/16 inch or about ⅛×¼×¼ inch.

EXAMPLE 1

| Ingredients | |
|---|---|
| Carrier "A" | 70.91 grams |
| Ethylenediamine (High Purity Grade) | 30.33 grams |
| Distilled Water | 30.0 grams |
| Oxalic Acid Dihydrate (Reagent Grade) | 30.38 grams |
| Silver Oxide Powder (Metz) | 53.21 grams |
| Monoethanolamine, Fe + Cl free | 10.62 grams |
| $CsMnO_4$ | 0.0674 grams |
| $KMnO_4$ | 0.0212 grams |
| $H_2SO_4$ solution (0.011374 g $SO_4^{-2}$/g solution) | 1.57 grams |
| Distilled water | 51.49 grams |
| Properties of Carrier "A" utilized in Example 1 are the following: | |
| Apparent Porosity (%) | 65.6 |
| % Water Absorption | 50.0 |
| Attrition Loss/Hr. (%) | 14.8 |
| 25 Ft. Drop Test (% Passing) | 99 |
| Crush Strength Average, lbs. | 20.1 |
| Crush Strength Range, lbs. | 7–29 |
| Surface Area, $M^2/g$ | 0.497 |
| Total Pore Volume (cc/g) | 0.514 |
| Pore Size (Microns) | |
| $P_1$ (less than 0.1) | 1.5% |
| $P_2$ (0.1–0.5) | 3.0% |
| $P_3$ (0.5–1.0) | 10.0% |
| $P_4$ (1.0–10.0) | 29.0% |
| $P_5$ (10.0–100) | 51.0% |
| $P_6$ (greater than 100) | 5.5% |
| Average O.D. (.320 ± .031) in. | 100 |
| Ratio, Max/Min dia. (% 1.25) | 100 |
| Length, Long Side, % (.346 ± .046) in. | 99 |
| Average Long Side, in. | 0.337 |
| Packing Density, lbs/ft³ | 42.6 |
| Acid Leachable Sodium, ppm. | 903 |
| Acid Leachable Potassium, ppm. | 745 |
| Acid Leachable Calcium, ppm. | 530 |
| Acid Leachable Magnesium, ppm. | 30 |

A. Impregnation Solution Preparation

1. The ethylenediamine was mixed with distilled water.
2. Oxalic acid was slowly added to the aqueous ethylenediamine solution at ambient conditions. An exothermic reaction occurred and the solution temperature rose to about 40° C.
3. The silver oxide was then added slowly to the solution of step 2.
4. To the solution in 3 above was added the monoethanolamine. (Note: Steps 1 to 4 were performed in a batch 3 times the size set forth herein and then divided into three aliquoits one of which was used for the subsequent steps).
5. The alkali metal and acid were then added.
6. Distilled water was added to adjust the solution volume to 150 ml.

B. Impregnation Of Carrier "A"

1. 70.91 grams of Carrier "A" were evacuated at room temperature and the impregnation solution A above was added to Carrier "A" under vacuum.
2. The excess solution was drained off.

C. Catalyst Roasting

1. The impregnation carrier was roasted in hot air using a belt roaster at about 500° C. for 2.5 minutes over a belt roaster. Air flow was 66 SCFH/in².
2. The finished catalyst weighed 81.78 grams and was calculated to contain 13.25 wt. % silver, 0.00953 wt. % cesium, 0.00280 wt. % potassium and 0.00476 wt. % $SO_4^{-2}$.

The catalyst of Example 1 tested at STANDARD ETHYLENE OXIDE PROCESS CONDITIONS under oxygen conditions (6.7 percent carbon dioxide) gave an efficiency of 76.0 percent at 254° C.

EXAMPLES 2 THROUGH 26

These examples demonstrate the addition of various oxyanion salts of cesium and other alkali and alkaline earth metals to various carriers according to the general recipe and procedure of Example 1. Table I below summarizes the details about the catalyst and the efficiencies at CONDITIONS. It should be appreciated that the catalyst performance characterized in these examples were not reflective of optimization of catalyst formation.

TABLE I

| Example No. | Silver wt % | Cs. ppm | Anion | Other Cation Metal | Other Cation Metal ppm | Other Anion Addition | Other Anion, ppm | Carrier | Efficiency % | Temp °C. |
|---|---|---|---|---|---|---|---|---|---|---|
| 2[a] | 13.4 | 301 | $Cs_2Ta_2O_6$ | $K_2SO_4$ | 41 | $H_2SO_4$ | 50 | C | 80.5 | 238 |
| 3[b] | 13.6 | 305 | $Cs_2Ta_2O_6$ | $K_2SO_4$ | 41 | $H_2SO_4$ | 50 | C | 79.6 | 237 |
| 4[c] | 13.0 | 282 | $Cs_2Ti_2O_6$ | $K_2SO_4$ | 38 | $H_2SO_4$ | 47 | D | 80.1 | 251 |
| 5[d] | 14.1 | 51 | $CsMnO_4$ | $KMnO_4$ | 152 | — | — | D | 54.6 | 281 |
| 6[e] | 13.7 | 294 | $Cs_2Ta_2O_6$ | $K_2Ta_2O_6$ | 86 | — | — | D | 74.7 | 265 |
| 7[f] | 17.9 | 280 | $Cs_2MoO_4$ | $K_2SO_4$ | 105 | — | — | H | 77.6 | 267 |
|  |  | 50 | $Cs_2SO_4$ | $Ba(NO_3)_2$ | 55 |  |  |  |  |  |
| 8[g] | 31* | 40 | $Cs_3PO_4$ | — | — | — | — | L | 82.3 | 240 |
| 9[h] | 31* | 60 | $Cs_2Ta_2O_6^2$ | — | — | — | — | K | 82.6 | 241 |
|  |  | 140 | $Cs_2MoO_4$ |  |  |  |  |  |  |  |
|  |  | 750 | $Cs_2SO_4$ |  |  |  |  |  |  |  |
| 10[i] | 30* | 220 | $CsMnO_4$ | — | — | — | — | K | 81.5 | 229 |
|  |  | 140 | $Cs_2MoO_4$ |  |  |  |  |  |  |  |
|  |  | 750 | $Cs_2SO_4$ |  |  |  |  |  |  |  |
| 11[j] | 17 | 600 | $Cs_2SO_4$ | — | — | $NH_4ReO_4$ | 261 | M | 86 | 250 |
|  |  | 400 | CsOH |  |  |  |  |  |  |  |
| 12[k] | 17 | 600 | $Cs_2SO_4$ | — | — | $NH_4ReO_4$ | 131 | M | 86 | 260 |
|  |  | 200 | CsOH |  |  |  |  |  |  |  |
|  |  | 200 | $Cs_2MoO_4$ |  |  |  |  |  |  |  |
| 13[l] | 30* | 200 | $Cs_2MoO_4$ | — | — | — | — | J | 84.4 | 238 |

TABLE I-continued

| Example No. | Silver wt % | Cs. ppm | Anion | Other Cation Metal | Other Cation Metal ppm | Other Anion Addition | Other Anion, ppm | Carrier | Efficiency % | Temp °C |
|---|---|---|---|---|---|---|---|---|---|---|
| | | 800 | Cs$_2$SO$_4$ | | | | | | | |
| 14$^m$ | 32* | 200 | Cs$_2$MoO$_4$ | — | — | — | — | K | 85.5 | 248 |
| | | 750 | Cs$_2$SO$_4$ | | | | | | | |
| | | 60 | Cs$_2$WO$_4$ | | | | | | | |
| 15$^n$ | 32* | 140 | Cs$_2$MoO$_4$ | — | — | — | — | K | 83.3 | 254 |
| | | 750 | Cs$_2$SO$_4$ | | | | | | | |
| | | 60 | Cs$_2$CrO$_4$ | | | | | | | |
| 16$^o$ | 13 | 50 | Cs$_2$MoO$_4$ | — | — | — | — | A | 76.7 | 266 |
| | | 150 | Cs$_2$SO$_4$ | | | | | | | |
| 17$^p$ | 30* | 100 | Cs$_2$MoO$_4$ | — | — | (NH$_4$)$_2$MoO$_4$ | 60 | J | 83.7 | 235 |
| | | 750 | Cs$_2$SO$_4$ | | | | | | | |
| 18$^q$ | 31* | 355 | Cs$_2$MoO$_4$ | Rb$_2$SO$_4$ | 220 | — | — | E | 84.7 | 244 |
| | | 190 | Cs$_2$SO$_4$ | | | | | | | |
| 19$^r$ | 16 | 375 | Cs$_2$MoO$_4$ | — | — | — | — | F | 72.6 | 250 |
| | | 125 | CsNO$_3$ | | | | | | | |
| 20$^s$ | 14 | 120 | Cs$_2$MoO$_4$ | — | — | — | — | A | 82.0 | 234 |
| | | 140 | Cs$_2$SO$_4$ | | | | | | | |
| 21$^t$ | 14 | 206 | Cs$_2$WO$_4$ | — | — | — | — | A | 82.2 | 230 |
| | | 165 | Cs$_2$SO$_4$ | | | | | | | |
| 22$^u$ | 30* | 52 | Cs$_2$CrO$_4$ | — | — | — | — | J | 82.5 | 227 |
| | | 730 | Cs$_2$SO$_4$ | | | | | | | |
| 23$^v$ | 30* | 315 | Cs$_2$WO$_4$ | — | — | — | — | J | 85.2 | 228 |
| | | 840 | Cs$_2$SO$_4$ | | | | | | | |
| 24$^w$ | 20 | 244 | Cs$_2$SO$_4$ | — | — | NH$_4$F | 117 | N | 82.7 | 220 |
| | | 98 | Cs$_2$MoO$_4$ | | | | | | | |
| 25 | 10.5 | 96 | Cs$_2$WO$_4$ | K$_2$CO$_3$ | 28 | — | — | I | 69.7 | 263 |
| 26 (Comparative) | 10.5 | 96 | CsOH | K$_2$CO$_3$ | 28 | — | — | I | 69.4 | 258 |

*Prepared in two impregnations with 10 wt. % Ag added in the first impregnation. For catalysts prepared from three cesium sources, 50% of the cesium sources (except Cs$_2$SO$_4$) were added in the first impregnation.
$^a$Roasted at 350° C., 15.6 ppm ethylene dichloride.
$^b$5.0 ppm ethyl chloride, 6.4% CO$_2$.
$^c$6.6% CO$_2$.
$^d$0.2% outlet EO, 5 ppm ethyl chloride, Air Conditions.
$^e$7.0 ppm ethyl chloride.
$^f$3.3 ppm ethyl chloride, 1.18% outlet EO, Air Conditions.
$^g$2.0 ppm ethyl chloride, 6.0% inlet carbon dioxide.
$^h$2.0 ppm ethyl chloride, 6.0% inlet carbon dioxide.
$^i$2.0 ppm ethyl chloride, 6.0% inlet carbon dioxide.
$^j$4.4 ppm ethyl chloride, 0.92% outlet EO.
$^k$6 ppm ethyl chloride, 0.61% outlet EO.
$^l$2.0 ppm ethyl chloride.
$^m$2.0 ppm ethyl chloride, 6.0% inlet carbon dioxide.
$^n$2.0 ppm ethyl chloride, 6% inlet carbon dioxide.
$^o$6.0 inlet carbon dioxide, 2.0% outlet EO, 7.5 ppm ethyl chloride.
$^p$2.0 ppm ethyl chloride.
$^q$1.9 ppm ethyl chloride.
$^r$1.5 ppm ethyl chloride, 0% carbon dioxide in inlet, 1.88% outlet EO.
$^s$2.5 ppm ethyl chloride.
$^t$2.5 ppm ethyl chloride, 11.3 standard cubic feet per hour flow velocity.
$^u$2.5 ppm ethyl chloride.
$^v$2.5 ppm ethyl chloride.
$^w$2.5 ppm ethyl chloride, 1.37% outlet EO, 11.3 standard cubic feet per hour flow velocity.

It is claimed:

1. A catalyst for the manufacture of ethylene oxide by the epoxidation of ethylene containing an impregnated silver metal on an inert, refractory solid support and an efficiency-enhancing amount, relative to the amount of silver metal of a mixture of cesium salts, at least one of which is a cesium salt in which the anion thereof is an oxyanion of an element having an atomic number of 21 to 75 and being from groups 3b through 7b, inclusive, of the Periodic Table of the Elements.

2. The catalyst of claim 1 in which at least one cesium salt is selected from the group of the manganates, tungstates, molybdates, vanadates, tantalates, titanates, zirconates and chromates.

3. The catalyst of claim 1 in which at least one cesium salt is a halide having an atomic number of 9 to 53 or an oxyanion of an element other than the oxygen therein having an atomic number of (i) 7 or (ii) 15 to 83 and being from groups 3a to 7a of the Periodic Table of the Elements.

4. The catalyst of claim 3 in which at least one cesium salt is cesium sulfate.

5. The catalyst of claim 3, in which at least one cesium salt is selected from the group of the manganates, tungstates, molybdates, vanadates, tantalates, titanates, zirconates and chromates.

6. The catalyst of claim 3 in which at least two cesium salts are oxyanions of elements having an atomic number of 15 to 83 and being from groups 3b to 7b, inclusive, and 3a to 7a, inclusive, of the Periodic Table of the Elements.

7. The catalyst of claim 1 in which at least two cesium salts are oxyanions of elements having an atomic number of 15 to 83 and being from groups 3b to 7b, inclusive, and 3a to 7a, inclusive, of the Periodic Table of the Elements.

8. The catalyst of claim 1 in which the cesium salts comprise said oxyanions and halides.

9. The catalyst of claim 1 in which the support is alpha-alumina.

10. The catalyst of claim 9 in which at least two cesium salts are oxyanions of elements having an atomic number of 15 to 83 and being from groups 3b to 7b, inclusive, and 3a to 7a, inclusive, of the Periodic Table of the Elements.

11. The catalyst of claim 9 in which at least one cesium salt is selected from the group of the manganates, tungstates, molybdates, vanadates, tantalates, titanates, zirconates and chromates.

12. The catalyst of claim 11 in which cesium salt comprises at least one of halide, sulfate and phosphate.

13. The catalyst of claim 12 in which the cesium salts having oxyanions of elements having atomic numbers of 21 to 75 and being from groups 3b to 7b of the Periodic Table of the Elements comprise at least about 30 mole percent of the total cesium salts.

14. The catalyst of claim 9 in which the cesium salts having oxyanions of elements having atomic numbers of 21 to 75 and being from groups 3b to 7b of the Periodic Table of the Elements comprise at least about 30 mole percent of the total cesium salts.

15. The catalyst of claim 14 which comprises cesium sulfate.

16. The catalyst of claim 9 in which at least one cesium salt comprises a manganate.

17. The catalyst of claim 9 in which at least one cesium salt comprises a tungstate.

18. The catalyst of claim 9 in which at least one cesium salt comprises a molybdate.

19. The catalyst of claim 9 in which at least one cesium salt comprises a vanadate.

20. The catalyst of claim 9 in which at least one cesium salt comprises a titanate.

21. The catalyst of claim 9 in which at least one cesium salt comprises a zirconate.

22. The catalyst of claim 9 in which at least one cesium salt comprises a chromate.

23. The catalyst of claim 9 in which at least one cesium salt comprises a cerate.

24. The catalyst of claim 9 in which at least one cesium salt comprises a tantalate.

25. The catalyst of claim 9, wherein said catalyst has been subjected to a process for making ethylene oxide by the reaction of ethylene and oxygen.

26. The catalyst of claim 25, wherein the process to which the catalyst was subjected involves the use of a gas phase inhibitor.

27. The catalyst of claim 26 in which the gas phase inhibitor is an organic chloride.

28. The catalyst of claim 1, wherein said catalyst has been subjected to a process for making ethylene oxide by the reaction of ethylene and oxygen.

29. The catalyst of claim 28, wherein the process to which the catalyst was subjected involves the use of a gas phase inhibitor.

30. The catalyst of claim 29 in which the gas phase inhibitor is an organic chloride.

* * * * *

UNITED STATES PATENT AND TRADEMARK OFFICE
CERTIFICATE OF CORRECTION

PATENT NO. : 5,057,481

DATED : October 15, 1991

INVENTOR(S) : M.M. Bhasin

It is certified that error appears in the above-identified patent and that said Letters Patent is hereby corrected as shown below:

In column 3, line 53, change the word "alpha alumina" to read --alpha-alumina--.

In column 4, line 49, change the word "alpha alumina" to read --alpha-alumina--.

In column 11, line 23, change the word "cc/q." to read --cc/g.--.

In column 11, line 47, change the word "alpha alumina," to read --alpha-alumina,--.

In column 16, line 19, after the word "ethylene" insert --oxide is separated and recovered from the reaction--.

Column 18, line 32, change the word "alpha Alumina" to read --alpha-Alumina--.

Column 25, line 54 in Table I, change the formula in the Anion column "$Cs_2Ti_2O_6$" to read --$Cs_2Ti_2O_3$--.

Column 25, line 59 insert the following under the "8S 3I* 40" entry --200 $Cs_2MoO_4$--.

UNITED STATES PATENT AND TRADEMARK OFFICE
CERTIFICATE OF CORRECTION

PATENT NO. : 5,057,481

DATED : October 15, 1991

INVENTOR(S) : M.M. Bhasin

Page 2 of 2

It is certified that error appears in the above-indentified patent and that said Letters Patent is hereby corrected as shown below:

Column 25, line 60 insert --750 $Cs_2SO_4$-- after the entry "200 $Cs_2MoO_4$".

Signed and Sealed this

Nineteenth Day of October, 1993

Attest:

BRUCE LEHMAN

*Attesting Officer*     *Commissioner of Patents and Trademarks*